United States Patent [19]

Tumanov et al.

[11] 4,222,666

[45] Sep. 16, 1980

[54] APPARATUS FOR MEASURING AND CORRECTING CALIBRATION CHARACTERISTIC OF PHOTOELECTRIC AEROSOL ANALYZER

[76] Inventors: Evgeny S. Tumanov, ulitsa Shelkovichnaya, 184, kv. 48; Nikolai V. Zhamkov, ulitsa Mokhovaya, 33/1; Lev A. Kudryavtsev, ulitsa Shelkovichnaya, 182, kv. 72, all of Saratov, U.S.S.R.

[21] Appl. No.: 924,098

[22] Filed: Jul. 12, 1978

[30] Foreign Application Priority Data

Jul. 13, 1977 [SU] U.S.S.R. .................................. 2508561

[51] Int. Cl.$^2$ ............................................. G01N 21/22
[52] U.S. Cl. ................................... 356/243; 356/336; 356/339
[58] Field of Search ............... 356/336, 339, 346, 243; 250/564, 565, 574

[56] References Cited

U.S. PATENT DOCUMENTS

| | | | |
|---|---|---|---|
| 3,506,359 | 4/1970 | Burke et al. .................. | 250/574 X |
| 3,869,208 | 3/1975 | Lorenz .......................... | 356/336 |

*Primary Examiner*—John K. Corbin
*Assistant Examiner*—Matthew W. Koren

*Attorney, Agent, or Firm*—Fleit & Jacobson

[57] ABSTRACT

An apparatus for measuring and correcting the calibration characteristic of a photoelectric aerosol analyzer comprises a light guide disposed within a nozzle of the analyzer and having its one end arranged in the analyzer, said end face being made as a ball to provide for an even distribution of the light flux in the working zone of the analyzer. There are provided a controllable light pulse generator, adapted to measure and correct the calibration characteristic of the analyzer, and a meter to measure the intensity of the light flux in the working zone, said generator and said meter being installed, one at a time, above the other, flat, end face of the light guide. The controllable light pulse generator has a housing accomodating a light chopper with a gauged hole and a light source installed before the light chopper so that the light beam from the light source passes through the gauged hole and impinges on the flat end face of the light guide, a light adjuster electrically coupled to the light source, and an electric motor mechanically coupled to the light chopper. The light flux meter comprises a serial arrangement including a light-sensitive receiver coupled optically to the flat end face of the light guide, a direct voltage source, both installed in the housing of the light flux meter, and a galvanometer.

4 Claims, 4 Drawing Figures

APPARATUS FOR MEASURING AND CORRECTING CALIBRATION CHARACTERISTIC OF PHOTOELECTRIC AEROSOL ANALYZER

FIELD OF THE INVENTION

The invention relates to metrology, and more particularly to apparatus for measuring and correcting the calibration characteristic of a photoelectric aerosol analyzer.

The invention can be used to measure and correct the calibration characteristic of the analyzers which measure the dust content of the air in mines, in workshops for precision assembly work and in other premises.

DESCRIPTION OF THE PRIOR ART

At present, more stringent requirements are imposed on the cleanness of industrial and business premises, which results in a wider use of photoelectric aerosol analyzers, capable of detecting the purity of air rapidly and with a high degree of validity. Verification of the photoelectric aerosol analyzers with a greater validity and accuracy can be attained when all their output parameters are checked and when their calibration characteristic is restored completely. This, in turn, necessitates more advanced means for measuring and correcting the calibration characteristic of such analyzers.

Known in the art is a device for measuring and correcting the calibration characteristic of a photoelectric aerosol analyzer (cf. the technical papers, certificate, description and operation manual, relating to "Photoelectric Counter for Aerosol Particles, Type AZ-5", issued by Tekmashexport, USSR, Moscow), said analyzer having a nozzle as well as a light source and a light-sensitive receiver between which an optical coupling is established at the moment that an aerosol particle under measurement passes through the nozzle, said device comprises a light chopper with a gauged hole, an electric motor mechanically connected with the light chopper, and a light guide to provide an optical coupling between the device and the analyzer.

The described device uses, however, a noncontrollable light source of the photoelectric aerosol analyzer proper with the result that only a certain point on the calibration curve can be restored which corresponds to an aerosol particle of a certain diameter. Thus, the aerosol particles belonging to a given diameter range cannot be measured with an adequate validity and great measurement errors therefore take place.

Moreover, the described device is able to check only the circuit incorporating the light source of the analyzer and it therefore fails to detect locations in other analyzer subassemblies at which errors might occur with the result that the total measurement error is increased.

Finally, the described device is part of the analyzer proper and requires functional check during the operation. This functional check cannot be performed since the device, due to its design features, necessitates specific optical adjustment in this case and no coupling can be established between it and reference measurement apparatus.

SUMMARY OF THE INVENTION

An object of the invention is to provide an apparatus for measuring and correcting the calibration characteristic of photoelectric aerosol analyzers, which apparatus has an increased accuracy of verification of the analyzers.

Another object of the invention is to provide for an increased accuracy of verification of photoelectric aerosol analyzers.

Still another object of the invention is to provide for determination of component errors of photoelectric aerosol analyzers.

Yet another object of the invention is to reduce the level of optical noise occurred in the proposed apparatus.

Another object of the invention is to reduce the time required for the verification of photoelectric aerosol analyzers.

There is disclosed an apparatus for measuring and correcting the calibration characteristic of a photoelectric aerosol analyzer which has a nozzle and a light source and a light-sensitive receiver between which an optical coupling is established at the moment that an aerosol particle under measurement passes through the nozzle. The apparatus comprises a light chopper, an electric motor mechanically connected with the light chopper, and a light guide to provide an optical coupling between the apparatus and the photoelectric aerosol analyzer. The light guide, according to the invention, is disposed within said nozzle and has its one end face arranged in the photoelectric aerosol analyzer and made as a ball to provide for even distribution of the light flux in the working zone of the photoelectric aerosol analyzer. The apparatus further comprises a controllable light pulse generator to measure and correct the calibration characteristic of the photoelectric aerosol analyzer and a meter to measure the intensity of the light flux in the working zone of the photoelectric aerosol analyzer, the controllable light pulse generator and the light flux meter being adapted to be installed, one at a time, above the other, flat, end face of the light guide, the controllable light pulse generator having a housing accomodating the light chopper in front of which there is provided a light source so that the light flux, when passed through the gauged hole of the light chopper, impinges on the flat end face of the light guide, and a light adjuster electrically coupled to the light source of the generator, and the light flux meter having a serial arrangement including a light-sensitive receiver and a direct voltage source, both disposed in the housing of the meter, and a galvanometer.

Advantageously, the housing of the controllable light pulse generator and the housing of the light flux meter each have a bush adapted to mechanically connect its respective housing to the housing of the light guide, the axis of the bush being aligned with the optical axis of the light guide.

Preferably, the inner surface of the light chopper facing the light source of the controllable light pulse generator has a light-absorbing coating.

The instant invention makes it possible to measure the calibration characteristic within the overall range of size of aerosol particles, thereby providing for an increased accuracy of verification of photoelectric aerosol analyzers.

The invention provides for a decreased level of optical noise, which results in an increase in the range of size of the simulated aerosol particles to cover the descending portion of the range.

The invention makes it possible to determine circuit locations at fault, which allows for the detection of the component errors of photoelectric aerosol analyzers.

With the invention, it is possible to use the light pulses which simulate the passage of the actual aerosol particles through photoelectric aerosol analyzers so as to avoid a labor-consuming technique in which the actual aerosol particles are used in checking such analyzers.

DESCRIPTION OF THE DRAWINGS

The invention will now be described, by way of example, with reference to the accompanying drawings in which.

DESCRIPTION OF THE INVENTION

Figure 1:
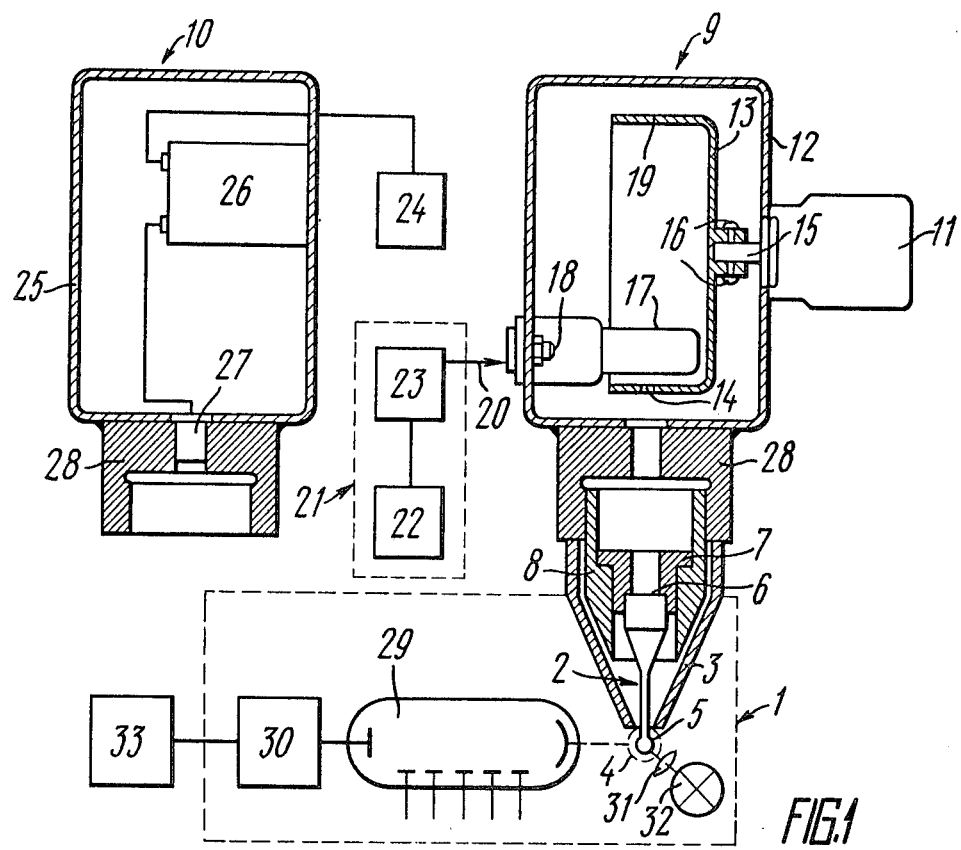
FIG. 1 is a general diagrammatic representation of an apparatus for measuring and correcting the calibration characteristic of a photoelectric aerosol analyzer, according to the invention.

The apparatus of the invention for measuring and correcting the calibration characteristic of a photoelectric aerosol analyzer 1 (FIG. 1) comprises a light guide 2 disposed within a nozzle 3 of the analyzer 1. One end face of the light guide 2, disposed in the analyzer 1 at the center of a working zone 4, is made as a ball 5 to provide for even distribution of the light flux in the working zone 4. The other, flat, end face 6 of the light guide 2 is set in a hollow cylindrical mount 7. The light guide 2 with the mount 7 is fixed in a housing 8.

The apparatus of the invention also comprises a controllable light pulse generator 9 and a meter 10 to measure the intensity of the light flux in the working zone 4 of the analyzer 1, said controllable light pulse generator 9 and said light flux meter 10 being installed, one at a time, above the flat end face 6. The controllable light pulse generator 9 comprises an electric motor 11 and a light chopper 13 with a gauged hole 14, disposed in a housing 12 and attached to a shaft 15 of the electric motor 11 with bolts 16. The light chopper 13 is made as a sleeve accomodating a light source 17 fixed to the housing 12 with a bolt 18 so that the light flux from the light source 17 passes through the gauged hole 14 and impinges on the flat end face 6. The inner surface of the light chopper 13 facing the light source 17 has a light-absorbing coating 19. A light adjuster 21 is comprised of a current source 22 and an ammeter 23, the output of which is an output 20 of the light adjuster 21, which is coupled to the light source 17. The light flux meter 10 includes a serial arrangement comprising a galvanometer 24 and a direct voltage source 26 and a light-sensitive receiver 27, both installed in a housing 25 of the light flux meter 10. Housings 12 and 25 of the controllable light flux generator 9 and the light flux meter 10, respectively, each have a bush 28 (FIGS. 1, 2) which is disposed, with the generator 9 (FIG. 1) and the light flux meter 10 (FIG. 2) in the operating position, in the housing 8 (FIGS. 1,2) of the light guide 2, the axis of the bush 28 being aligned with the optical axis of the light guide 2. The analyzer 1 also has a light-sensitive receiver 29 located in close proximity to the working zone 4 and connected to a pulse amplifier 30. An objective 31 is available, the focal length of which is measured from the center of the working zone 4, and a light source 32 is set before the objective 31. A pulsed voltmeter 33 is connected to the pulse amplifier 30.

Figure 2:
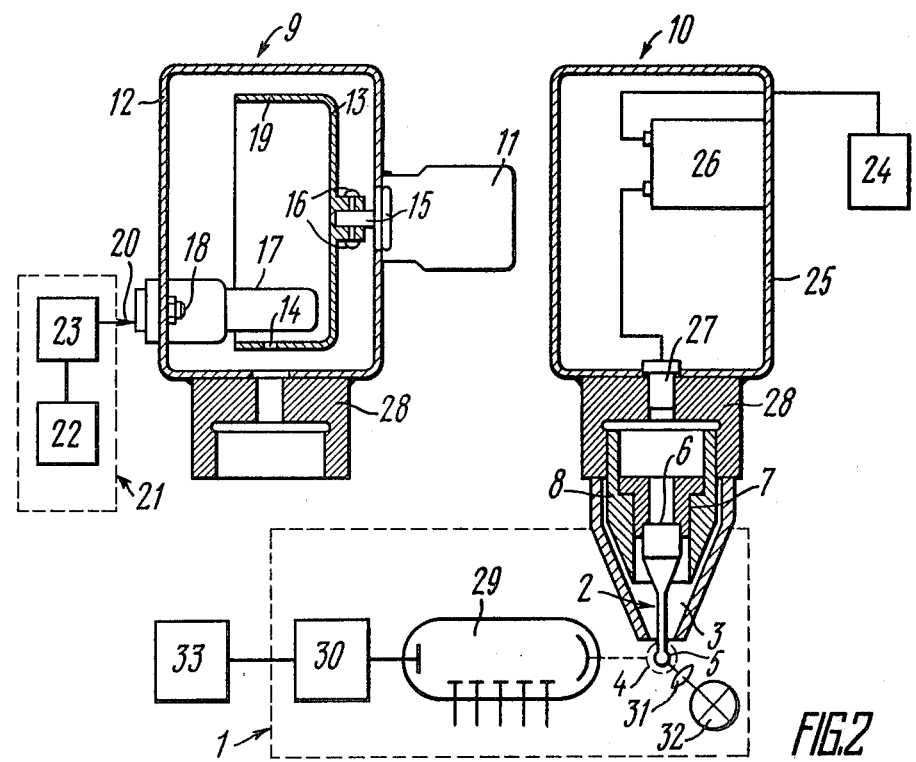
FIG. 2 is a general diagrammatic representation of the apparatus for measuring and correcting the calibration characteristic of the photoelectric aerosol analyzer to show the measurement of the intensity of the light flux in the working zone of the analyzer, according to the invention.

FIG. 2 shows a diagrammatical representation of the apparatus of invention to measure the intensity of the light flux in the working zone 4 of the analyzer 1. In this case, the light flux meter 10 is installed above the flat end face 6 and the bush 28 of the housing 25 fits over the housing 8 of the light guide 2.

Figure 3:
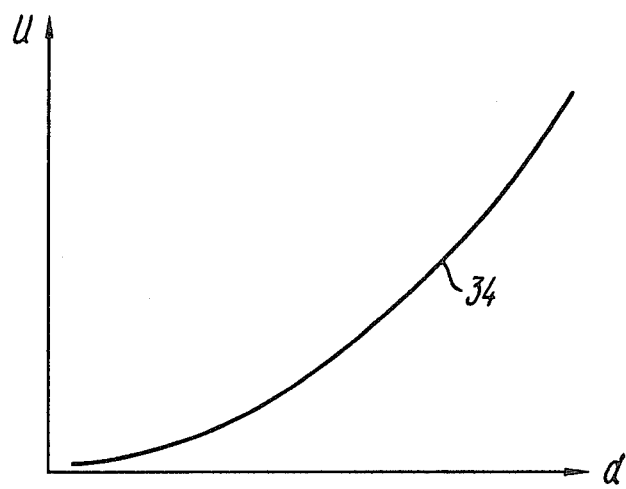
FIG. 3 shows the reference calibration characteristic of the photoelectric aerosol analyzer, according to the invention.
Figure 4:
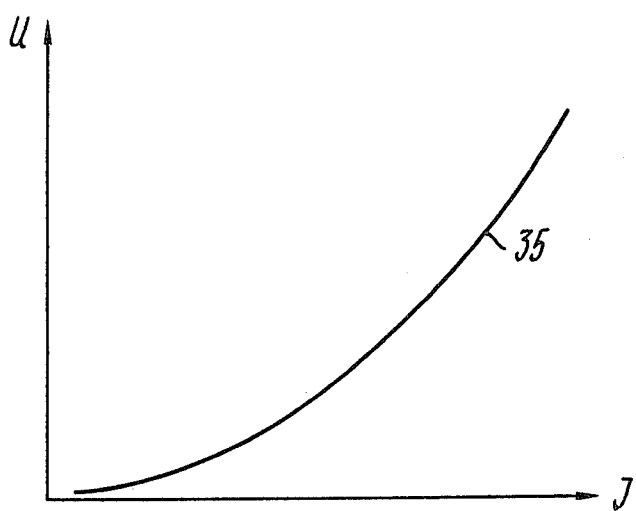
FIG. 4 shows the measured calibration characteristic of the photoelectric aerosol analyzer, according to the invention.

The apparatus of the invention operates in the following manner. The light source 32 (FIGS. 1, 2) of the photoelectric analyzer 1 to be checked by the apparatus of the invention produces a light beam focused at the center of the working zone 4. The aerosol particles passing through the nozzle 3 enter the light beam and tend to reflect and disperse the light pulses, the duration of which is determined by the time interval within which the particles come through the working zone 4. These light pulses are sensed by the light-sensitive receiver 1 and converted to electrical pulses having amplitude U proportional to the size of the particles passing through the working zone 4. The relationship between amplitude U produced by the pulse amplifier 30 and registered by the pulsed voltmeter 30 and diameter d of the aerosol particles represents the reference calibration characteristic (curve) 34 of the analyzer 1 (FIGS. 1, 2) as shown in FIG. 3.

Before the measurement and correction of the calibration characteristic commences, the ball 5 of the light guide 2 fixed in the housing 8 with the help of the mount 7 is introduced in the working zone 4.

In order to measure the intensity of the light flux in the working zone 4 (FIG. 2), the housing 25 of the light flux meter 10 is set on the housing 8 of the light guide 2 with the help of the bush 28.

The light beam produced by the light source 32 impinges on the ball 5 and is transmitted by the light guide 2 to the light-sensitive receiver 27 coupled in series with the direct voltage source 26 and the galvanometer 24. The latter reads the value of the component of the reference calibration characteristic 34 (FIG. 3) corresponding to the circuit of the light source 32 (FIG. 2) including the working zone 4. After that, the light source 32 is turned off.

In order to measure and correct the calibration characteristic of the photoelectric aerosol analyzer 1 (FIG. 1), the housing 12 of the controllable light pulse generator 9 is installed on the housing 8 of the light guide 2 with the help of the bush 28.

When energized by the light adjuster 21, the light source 17 produces a light beam passing through the gauged hole 14 of the light chopper 13 rotated by the electric motor 11 at a preset speed. The light beam impinges on the flat end face 6 of the light guide 2 and is then passed to the ball 5. The light pulses produced by the light chopper 13 are distributed by the ball 5 in even manner over the working zone 4, sensed by the light-sensitive receiver 29 and converted in it to electrical pulses which are amplified by the pulse amplifier 30 and registered by the pulsed voltmeter 33. The relationship between amplitude U of the electric pulses and current I of the light source 17, adjusted by the light adjuster 21, represents the measured calibration characteristic 35 of the analyzer 1 (FIG. 1) as shown in FIG. 4. When the measured calibration characteristic 35 (FIG. 4) of the analyzer 1 (FIG. 1) deviates from the reference calibration characteristic 34 (FIG. 3) of the analyzer 1 (FIG. 1), the light-sensitive receiver 27 (FIG. 1) and the pulse amplifier 30 are used to correct the measured calibration characteristic 35 (FIG. 4) within the overall range of the size of the aerosol particles being measured.

The proposed apparatus itself can be checked using reference measuring means. This allows the parameters of the apparatus and, therefore, the accuracy of measurement and correction of the calibration characteristic of photoelectric aerosol analyzers to be kept constant during the entire service life of the apparatus.

What is claimed is:

1. An apparatus for measuring and correcting the calibration characteristic of a photoelectric aerosol analyzer having a nozzle and a light source and a light-sensitive receiver between which an optical coupling is established at the moment that an aerosol particle under measurement passes through said nozzle, said apparatus comprising:

light guide means disposed within said nozzle and having a first end face located in said photoelectric aerosol analyzer and made as a ball for providing an even distribution of the light flux in a working zone of said analyzer, said light guide means having a second, flat, end face;

controllable light pulse generator means installed above said flat end face of said light guide means for measuring and correcting the calibration characteristic of the photoelectric aerosol analyzer;

a housing of said controllable light pulse generator means;

a light chopper of said controllable light pulse generator means having a gauged hole and an inner surface and disposed within said housing of said controllable light pulse generator means;

a light source of said controllable light pulse generator means installed in said housing of said controllable light pulse generator means in front of said light chopper so that the light flux produced by said light source passes through said gauged hole of said light chopper and impinges on said flat end face of said light guide means;

a light adjuster of said controllable light pulse generator means having an output electrically coupled to said light source of said controllable light pulse generator means;

an electric motor of said controllable light pulse generator means having a shaft mechanically coupled with said light chopper;

light flux meter means for measuring the intensity of the light flux in the working zone of said photoelectric aerosol analyzer, and installed above said flat end face of said light guide means to effect the measurement;

a housing of said light flux meter means;

a light-sensitive receiver of said light flux meter means disposed within said housing of said light flux meter means and coupled optically to said flat end face of said light guide means;

a direct voltage source of said light flux meter means having an input and an output, and disposed within said housing of said light flux meter means and having said output coupled to said light-sensitive receiver of said light flux meter means; and a galvanometer of said light flux meter means having an input coupled to said output of said direct voltage source.

2. An apparatus as claimed in claim 1, wherein said housing of said controllable light pulse generator means and said housing of said light flux meter means each have a bush which provides for mechanical connection of each of said housings with said housing of said light guide, means the axis of the bush being aligned with the optical axis of the light guide means.

3. An apparatus as claimed in claim 1, wherein said inner surface of said light chopper faces said light source of said controllable light pulse generator means and has a light-absorbing coating.

4. An apparatus as claimed in claim 2, wherein said inner surface of said light chopper faces said light source of said controllable light pulse generator means and has a light-absorbing coating.

* * * * *